United States Patent
Heitmeiter et al.

(10) Patent No.: US 9,352,083 B2
(45) Date of Patent: May 31, 2016

(54) DRIVE DEVICE FOR THE LINEAR MOVEMENT OF AN INFUSION SYRINGE PISTON, INFUSION PUMP AND METHOD FOR REPLACING AN INFUSION SYRINGE

(75) Inventors: Rolf Heitmeiter, Baunatal (DE); Rene Wildner, Melsungen (DE); Hans-Josef Gerlach, Marsberg (DE)

(73) Assignee: B. BRAUN MELSUNGEN AG, Melsungen (DE)

( * ) Notice: Subject to any disclaimer, the term of this patent is extended or adjusted under 35 U.S.C. 154(b) by 0 days.

(21) Appl. No.: 14/359,506

(22) PCT Filed: Aug. 7, 2012

(86) PCT No.: PCT/EP2012/065449
§ 371 (c)(1),
(2), (4) Date: Oct. 6, 2014

(87) PCT Pub. No.: WO2013/079226
PCT Pub. Date: Jun. 6, 2013

(65) Prior Publication Data
US 2015/0094665 A1    Apr. 2, 2015

(30) Foreign Application Priority Data
Nov. 30, 2011 (EP) .................................. 11181527

(51) Int. Cl.
*A61M 5/14* (2006.01)
*A61M 5/145* (2006.01)

(52) U.S. Cl.
CPC ............ *A61M 5/1456* (2013.01); *A61M 5/1458* (2013.01); *A61M 2205/3306* (2013.01)

(58) Field of Classification Search
CPC ............ A61M 5/1456; A61M 5/1458; A61M 5/16831; G01L 1/142
See application file for complete search history.

(56) References Cited

U.S. PATENT DOCUMENTS

| 5,879,360 A | 3/1999 | Crankshaw |
| 2009/0005730 A1 | 1/2009 | Gerlach et al. |
| 2012/0215170 A1 | 8/2012 | Traversaz et al. |

FOREIGN PATENT DOCUMENTS

| CN | 1433816 | 8/2003 |
| EP | 0 514 907 | 11/1992 |

(Continued)

OTHER PUBLICATIONS

Translation of Communication of EP 11 18 1527 dated Sep. 21, 2012.
(Continued)

*Primary Examiner* — Scott Medway
(74) *Attorney, Agent, or Firm* — RatnerPrestia (57) ABSTRACT

The invention relates to a drive device for linear movement of an infusion syringe piston of an infusion syringe disposed on an infusion pump comprising a drive head unit including a main bearing means for supporting the infusion syringe piston, a fixing means for securing the infusion syringe piston to the main bearing unit as well as means for triggering the fixing means and comprising an advancing means for the drive head unit including a motor-drivable advancing spindle and a multi-part advancing spindle nut having at least one radially movable nut shell, wherein the drive head unit additionally comprises detecting means for detecting the infusion syringe piston ahead of the main bearing means, the detecting means including a multi-threshold sensor unit comprising an at least two-stage upstream detection means for detecting different positions of the infusion syringe piston ahead of the main bearing means.

16 Claims, 3 Drawing Sheets

(56) References Cited

FOREIGN PATENT DOCUMENTS

| | | | |
|---|---|---|---|
| EP | 1 110 569 | 6/2001 | |
| EP | 2093785 A1 * | 8/2009 | ............ H01H 25/04 |
| WO | WO 95/20145 | 7/1995 | |
| WO | WO 2011/039250 | 4/2011 | |

OTHER PUBLICATIONS

International Search Report for PCT/EP2012/065449 mailed Sep. 21, 2012.

Chinese Office Action with Search Report and translation for CN201280059301.0 dated Aug. 5, 2015.

* cited by examiner

DRIVE DEVICE FOR THE LINEAR MOVEMENT OF AN INFUSION SYRINGE PISTON, INFUSION PUMP AND METHOD FOR REPLACING AN INFUSION SYRINGE

CROSS REFERENCE TO RELATED APPLICATIONS

This application is the U.S. national phase application of PCT International Application No. PCT/EP2012/065449 filed Aug. 7, 2012, which claims priority to European Patent Application No. EP 11181527.0 filed Nov. 30, 2011, the contents of each application being incorporated by reference herein.

FIELD OF THE INVENTION

The invention relates to a drive device for linear movement of an infusion syringe piston of an infusion syringe disposed on an infusion pump comprising a drive head unit including a main bearing means for supporting the infusion syringe piston, a fixing means for fixing the infusion syringe piston to the main bearing means as well as means for triggering the fixing means and comprising an advancing means for the drive head unit including a motor-drivable advancing spindle and a multi-part advancing spindle nut having at least one radially movable nut shell, wherein the drive head unit additionally includes a detection means for detecting the infusion syringe piston ahead of the main bearing means.

Moreover, the invention relates to an infusion pump comprising a drive head unit for moving an infusion syringe piston of an infusion syringe disposed on the infusion pump and comprising an advancing means for driving the drive head unit.

Furthermore, the invention relates to a method for replacing an infusion syringe on an infusion pump comprising a drive head unit for linear movement of an infusion syringe piston in which at least one radially movable nut shell of an advancing spindle nut is radially disengaged from an advancing spindle of an advancing means for driving the drive head unit so that the drive head unit of a piston plate of the infusion syringe piston can be quickly axially fed by hand and in which for preventing inadvertent bolus administration the piston plate is detected by a contact element associated with the drive head unit, before the piston plate enters into contact with a main bearing surface of a main bearing means of the drive head unit.

BACKGROUND

Generic drive devices and corresponding injection pumps are well known from the state of the art and have been successfully used in infusion therapy since long.

For example from WO 2011/039250 A1 a method for preventing inadvertent bolus administration regarding a manual feed movement of a slide means for an infusion syringe piston especially after replacing an infusion syringe on an infusion pump as well as the corresponding infusion pump are known. Apart from the slide means for sliding the infusion syringe piston, the infusion pump especially includes an infusion syringe seat for securing an infusion syringe, an advance comprising a two-part advancing spindle nut for driving the slide means as well as a means for blocking the manual infeed movement of the slide means. In this context, the advance excels by an advancing spindle and an advancing coupling for coupling or uncoupling the slide means with or from the advancing spindle, whereby in the uncoupled state of the coupling the slide means advantageously can be quickly manually fed to the infusion syringe piston of the newly inserted infusion syringe. Such quick manual feeding is of advantage especially in critical situations, when it is necessary to quickly administer a vital infusion to a patient. In order to be able to reduce the risk of a quite dangerous inadvertent bolus administration to the patient, however, the infusion pump is provided with a blocking means by which the manual infeed movement can be quickly inhibited, when the slide means has been manually fed sufficiently closely to the infusion syringe piston. In particular, the blocking means excels by a check thread shaft juxtaposed to the advancing spindle and including a threaded shaft nut non-detachably corresponding thereto and by a braking means for the check thread shaft. The threaded shaft nut is tightly connected to the slide means so that the manual feed movement immediately blocks, when the braking means blocks rotation of the check thread shaft. The blocking means is controlled by a signal means associated with the slide means comprising at least one sensor at the slide means which is adapted to detect an approach of the slide means to the infusion syringe piston, the braking means blocking the check thread shaft, when a certain approach of the infusion syringe piston to the slide means is reached or exceeded. Hereby inadvertent or critical abutting against the infusion syringe piston in the course of quick manual feed movement can be reliably prevented. The blocking means includes an electromagnetic brake electrically connected to the signal means for blocking the check thread shaft.

SUMMARY

It is an object of the present invention to render replacement of an infusion syringe on an infusion pump simpler and nevertheless safer as regards the risk of inadvertent bolus administration to a patient.

An object of the invention is achieved, on the one hand, by a drive device for linear movement of an infusion syringe piston of an infusion syringe disposed on an infusion pump comprising a drive head unit including a main bearing means for supporting the infusion syringe piston, a fixing means for fixing the infusion syringe piston on the main bearing means as well as means for releasing the fixing means and comprising an advancing means for the drive head unit including a motor-drivable advancing spindle and a multi-part advancing spindle nut having at least one radially movable nut shell, wherein the drive head unit additionally comprises detecting means for detecting the infusion syringe piston ahead of the main bearing means, and wherein the detecting means includes a multi-threshold sensor unit comprising an at least two stage upstream detection means for detecting different positions of the infusion syringe piston ahead of the main bearing means.

The term "multi-threshold sensor unit" in accordance with the invention describes a means for detecting different positions of the infusion syringe piston arranged ahead of the drive head unit, and especially the piston plate thereof, before the infusion syringe piston bears on the main bearing means of the drive head unit with the piston plate.

In this case the multi-threshold sensor unit may consist of plural individual sensors arranged on or in the drive head unit and adapted to be functionally interconnected to form a sensor unit. Or else, the sensor unit consists of one single component in the casing of which at least two sensors are at least partly enclosed, depending on the structural design which can be built in a concrete configuration in a more advantageous manner.

Advantageously, by the multi-threshold sensor unit a cycle for proper start-up of an infusion pump especially after replacement of the infusion syringe can be automated at least in two stages, before the main bearing means can enter into contact with the piston plate of the infusion syringe piston, whereby the start-up of the infusion pump can be performed in a substantially more efficient and moreover more reliable manner.

This is due to the fact, on the one hand, that blocking of manual infeed of the drive head unit can be triggered with a first stage of the upstream detection means, wherein further infeed can then be continued immediately by a motor-driven infeed that is transferred ideally smoothly by a second stage of the prior detection means into a defined motor-driven reference travel in which the advancing spindle only carries out a defined number of revolutions. Hereby the drive head unit can be moved extremely rapidly, on the one hand, and extremely accurately, on the other hand, to the piston plate and can be placed at the piston plate ready for use.

In this respect, an object of the invention is also achieved, on the other hand, by a method for replacing an infusion syringe on an infusion pump comprising a drive head unit for linear movement of an infusion syringe piston in which at least one radially movable nut shell of an advancing spindle nut is radially disengaged from an advancing spindle of an advancing means for driving the drive head unit so that the drive head unit of a piston plate of the infusion syringe piston can be quickly axially fed by hand and in which for preventing inadvertent bolus administration the piston plate can be detected by a contact element associated with the drive head unit, before the piston plate enters into contact with a main bearing surface of a main bearing means of the drive head unit, wherein
- in a first detecting step the contact element triggers a first sensor element, thereby the manual infeed of the drive head unit with the advancing spindle nut and the advancing spindle being blocked by the at least one radially movable nut shell being radially engaged on the advancing spindle, wherein subsequently the drive head unit of the piston plate is continued to be fed by motor drive via the advancing means, in a second detecting step the contact element triggers a second sensor element, thereby a motor-driven reference travel of the drive head unit up to the main bearing surface of the main bearing means being initiated, and
- in a third detecting step in the course of contact of the piston plate with the main bearing surface the motor-driven reference travel is stopped and retaining brackets of a fixing means for the piston plate are closed, thereby the piston plate being secured to the main bearing means.

The reliability at an infusion pump can be further increased by said multiple detection without any delay occurring when the infusion syringe is replaced.

Advantageously the manual infeed of the drive head unit is blocked, before the contact element triggers the second sensor element. It can be especially ensured hereby that the advancing spindle nut is correctly locked at the advancing spindle, before the reference travel is initiated with the second sensor of the multi-threshold sensor unit as soon as said second sensor is appropriately triggered with the contact element. Thus the exact position of the drive head unit vis-à-vis the piston plate can always be guaranteed before the reference travel starts.

A preferred method variant provides that the motor-driven reference travel is carried out by way of a defined number of motor steps. By the defined number of motor steps an exactly predetermined number of revolutions of the advancing spindle and thus also a defined feeding path for the drive head unit can be realized especially on the last millimeters so that the drive head unit can always be placed especially exactly ahead of the piston plate.

As to construction, it is moreover especially advantageous when the multi-threshold sensor unit includes two sensors adapted to be triggered with one single transmitter element, the transmitter element comprising a contact element protruding from the main bearing means.

Since the mounting space at the drive head unit, especially at the main bearing means for a piston plate of the infusion syringe piston, are usually dimensioned to be very small, it is especially advantageous when the at least two sensors of the multi-threshold sensor unit can be triggered by only one single transmitter element.

Advantageously the contact element at the same time configures the transmitter element so that the drive head unit can have an even compacter design.

It is understood that the afore-mentioned sensors adapted to be triggered can be realized by the most different sensor means. For example Hall sensors can be used.

A structurally especially preferred design variant provides that the detecting means preferably comprises at least two light barriers which are arranged axially in series within the drive head unit. In particular, the two light barriers arranged in series can be addressed in especially simple construction with one single transmitter element.

Accordingly, the term "axially" means substantially aligned with the infeed motion of the drive head unit so that the actuating axis of the transmitter element advantageously coincides with the slide axis of the infusion syringe piston or is arranged in parallel thereto. So far the transmitter element advantageously can be simply formed to be identical to the contact element.

The drive head unit can be further structurally facilitated when at least one of the two light barriers is in the form of a fork light barrier.

Moreover, it is of advantage when the main bearing means includes a diaphragm plate comprising a transmitter element for switching sensors of the multi-threshold sensor unit comprising a contact element.

For example, a spring-biased diaphragm plate embodies at least one component or a component group of the means for triggering the fixing means for the piston plate. If then in said spring-biased diaphragm plate the multi-threshold sensor unit transmitter element is directly arranged, the design of the detecting means can be further facilitated.

Preferably the only transmitter element of the multi-threshold sensor unit is disposed within the means for triggering the fixing means so that especially the main bearing unit can have an even more compact design.

Another very advantageous design variant provides that one single transmitter element of the multi-threshold sensor unit has a pre-travel of a value between 2 mm and 10 mm, preferably of a value of 4 mm, before a first stage of the two-stage upstream detection means can be triggered by the only transmitter element. Such shortly selected pre-travel reduces the risk that with a too strong manual infeed motion the blocking means cannot react sufficiently quickly and the piston plate critically abuts against the main bearing means.

When the drive device includes at least one joint control means operating in response to the detecting means for automatic radial engagement of the at least one radially movable nut shell at the advancing spindle and for initiating a reference travel of the main bearing means adapted to be performed via the radially engaged advancing spindle nut up to the infusion piston, an interaction of these functions can be linked especially advantageously.

So as to obtain a drop of the power state and thus also of the magnetic fields at the two holding solenoids especially rapidly, it is of advantage when the control means comprises a comparator circuit unit for switching holding solenoids.

In this respect, it is of advantage when the advancing device comprises holding solenoids controllable with the detecting means for actuating axially displaceable sliding sleeves for radially engaging the advancing spindle nut relative to the advancing spindle.

Advantageously the risk of uncontrolled infusion can be further significantly reduced with the present invention despite a more rapid replacing possibility of an infusion syringe on an infusion pump.

The present infusion pump especially is a syringe pump in which at least one infusion syringe can be inserted. The present infusion pump can be operated both as individual pump and combined in a classification system or a docking station.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

The drive device 1 of an infusion pump 2 shown in FIGS. 1 to 7 substantially comprises a drive head unit 3 for moving a piston 4 of an infusion syringe 5 fastened to the infusion pump 2 and an advancing means 6 for the drive head unit 3.

The advancing means 6 substantially comprises an advancing slide 7, an advancing spindle 8 and a multi-part advancing spindle nut 9. Moreover the advancing means 6 further comprises an advancing motor and an appropriate gear which presently are not shown, however. By the advancing means 6 a linear feed movement of the drive head unit 3 is converted. The advancing slide 7 guarantees the linear guiding and the protection against torsion of the drive head unit 3.

The multi-part advancing spindle nut 9 and the advancing slide 7 can be driven forward when the direction of rotation of the advancing spindle 8 is appropriately selected in the piston driving direction 10, wherein especially the multi-part advancing spindle nut 9 is axially moved along the longitudinal extension 11 of the advancing spindle 8.

The multi-part advancing spindle nut 9 comprises a first radially movable nut shell 12 and a second radially movable nut shell 13, as will be described later in more detail. At any rate, the radially movable nut shells 12 and 13 can ensure axial form closure with the advancing spindle 8 and also reverse the same, however. For this, the two radially movable nut shells 12 and 13 in the advancing slide 7 are arranged to be supported in an engageable or disengageable manner vis-à-vis the advancing spindle 8.

The term "radially" characterizes a radial direction of movement 14 substantially transversely to the longitudinal extension 11 of the advancing spindle 8.

The advancing spindle 8 further has a male thread 15 by which the multi-part advancing spindle nut 9 can be positively connected.

The drive head unit 3 is fastened to the advancing slide 7 with a retaining arm 16 so that it is axially movable along with the advancing slide 7.

The drive head unit 3 moreover includes a main bearing means 17 for supporting a piston plate 18 of the infusion syringe piston 4. The piston plate 18 is supported on the main bearing means 17, when the infusion syringe piston 4 is displaced by the drive head unit 3 in the piston driving direction 10. The main bearing means 17 for this purpose configures a main bearing surface 19 on which the piston plate 18 is supported.

The piston plate 18 is fixed to the drive head unit 3 via a fixing means 20 so that a positive connection is guaranteed between the piston plate 18 of the infusion syringe piston 4 and the drive head unit 3.

Figure 2:
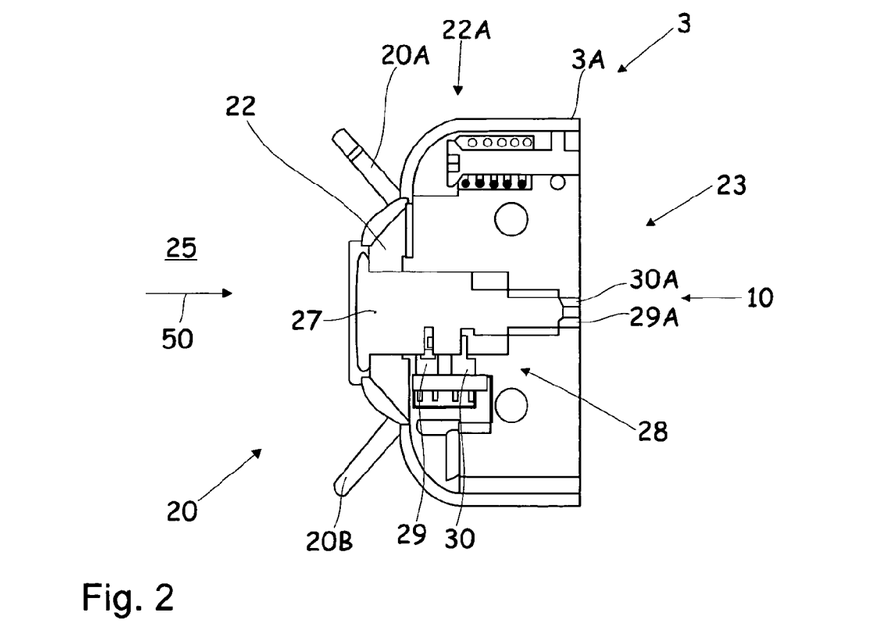
FIG. 2 schematically shows a longitudinally cut view of a front area of the drive head unit.
Figure 3:
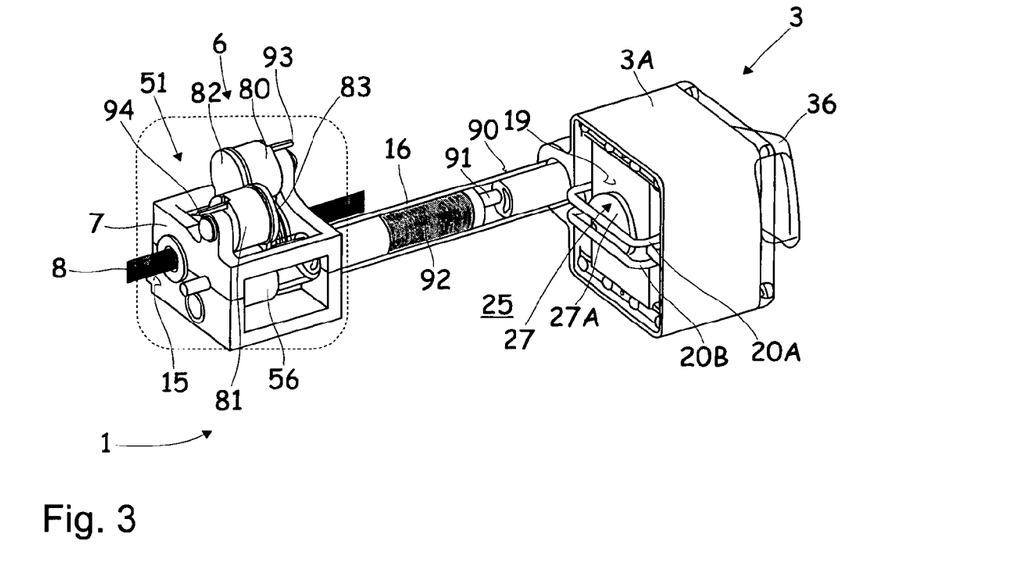
FIG. 3 schematically shows a perspective partly cut view of the drive device of the infusion pump from FIGS. 1 and 2 comprising the drive head unit and comprising the advancing unit for the same.

The fixing means 20 is equipped with means 21 for triggering the fixing means 20 comprising a diaphragm plate 22 which in turn provides a pressure sensor 22A with which an abutting pressure or a bearing pressure regarding the piston plate 18 vis-à-vis the main bearing means 17 can be detected. When a corresponding pressure is noticed, a movement of fixing brackets 20A and 20B of the fixing means 20 is triggered which then snap to the inside and fix the piston plate 18 to the main bearing surface 19 by form and force closure (FIGS. 2 and 4C).

While the means 21 for triggering the fixing means 20 especially with their diaphragm plate 22 and their pressure sensor 22A generally can be associated with detecting means 23 of the drive head unit 3, the detecting means 23 especially excels by a multi-threshold sensor unit 24 for detecting the infusion syringe piston 4 in the upstream area 25 of the main bearing means 17.

The detecting means 23 moreover includes a spring 26 biased axially displaceable transmitter element 27 for influencing the multi-threshold sensor unit 24. The transmitter element 27 is configured in a structurally simple manner directly by a contact element 27A of the drive head unit 3 which projects beyond the main bearing means 17 into the upstream area 25.

The multi-threshold sensor unit 24 excels by an at least two-stage upstream detection means 28 which is equipped with a first light barrier 29 and a second light barrier 30 axially arranged in series, whereby both of them can be influenced in a structurally especially simple manner by the only transmitter element 27.

While, on the one hand, the function of a drive gear 31 of the fixing means 20 can be controlled with the pressure sensor 22A of the diaphragm plate 22, on the other hand the function of the advancing means 6 can be influenced with the multi-threshold sensor unit 24, as will be described in more detail hereinafter. For this, the multi-threshold sensor unit 24 is connected to a control unit 33 of the advancing means 6 via an appropriate signal line 32.

Advantageously the drive device 1 further comprises a higher-level joint control means 34 operating as a function of the detecting means 23 for automatic radial engagement of the two radially movable nut shells 12 and 13 at the advancing spindle 8 and for initiating a reference travel of the main bearing means 17 adapted to be carried out with the radially engaged advancing spindle nut 9 up to the infusion syringe piston 4. The joint control means 34 is arranged in the upper part of an infusion pump housing 35 of the infusion pump 2 according to the representation in FIG. 1.

The joint control means 34 further excels by a comparator circuit unit 36 for switching holding solenoids 80 and 81, resp., (FIGS. 3, 5A and 5B) as will be described in more detail hereinafter.

Furthermore, at the drive head unit 3 a manually operable operating lever 36 is provided with which the functions of the fixing brackets 20A and 20B as well as of the advancing means 6 can be additionally manually operated. For mechanically operating the advancing means 6 with the operating lever 36, the latter is guided from the drive head unit 3 through the retaining arm 16 to the advancing means 6.

Figure 1:
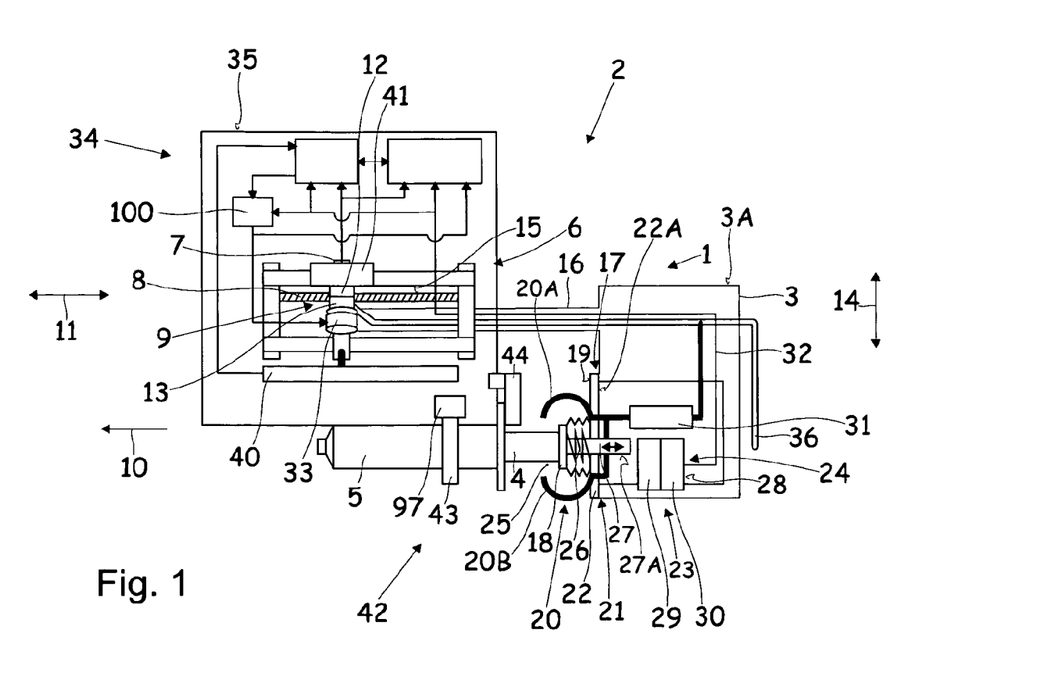
FIG. 1 schematically shows a view of an infusion pump comprising a drive device including a drive head unit having detecting means comprising a double-threshold sensor unit.

The control means 34 schematically illustrated especially in FIG. 1 shall be discussed here only in so far as the functions thereof are essential to the present invention. The control means 34 comprises, for example, a sensor 40 for determining a correct mounting position of the infusion syringe 5 and a form closure sensor 41 for checking a state of form closure between the multi-part advancing spindle nut 9 and the advancing spindle 8.

At the infusion pump housing 35 further a seat 42 for the infusion syringe 5 is provided to be accessible from outside, which seat includes a clamping bracket 43 for radially securing the infusion syringe 5 and a clamping lug 44 for axially securing the infusion syringe 5 at the seat 42 of the infusion pump 2.

In the view shown in FIG. 2 the drive head unit 3 is shown in greater detail. The detecting means 23 is clearly visible with its multi-threshold sensor unit 24 and the two-stage upstream detection means 28 which especially includes the two light barriers 29 and 30 axially arranged in series and the transmitter element 27 solely required for this purpose for reacting to the two light barriers 29 and 30, respectively.

Accordingly, the first light barrier 29 is electrically connected with a first electric cable connection 29A of the signal line 32 (FIG. 1) and the second light barrier 30 is electrically connected with a second electric cable connection 30A of the signal line 32 to the control means 34.

The transmitter element 27 in this representation is displaced into the drive head unit 3 due to contact with the piston plate 18 not shown here according to the arrow direction 50 so far that it has already disconnected the second light barrier 30. In so far the drive device 1 is in the second operating position 61 which will be explained in more detail hereinafter.

The transmitter element 27 of the two-stage upstream detection means 28 movably integrated in the diaphragm plate 22 which is supported to be movable relative to the diaphragm plate 22 is clearly visible.

Figures 4A, 4B:
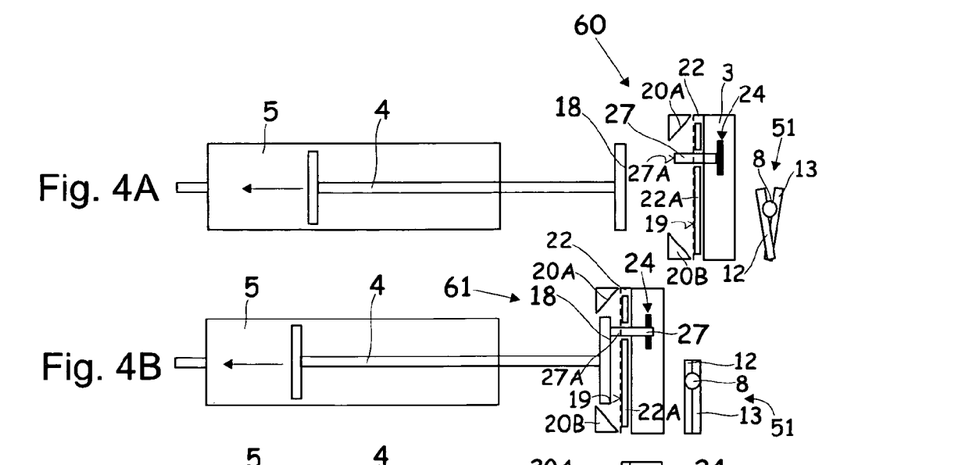
FIG. 4A schematically shows a view of a first operating position of the drive device from FIGS. 1 and 2 in which the drive head unit can be manually fed to a piston plate.
FIG. 4B schematically shows a view of a second operating position advanced vis-à-vis the first operating position from FIG. 4A in which a contact element of the detecting means has triggered a first threshold of the double-threshold sensor unit in the drive head unit.
Figure 4C:
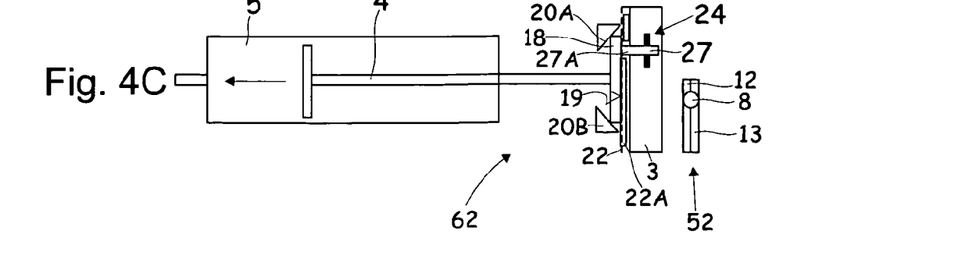
FIG. 4C schematically shows a view of a third operating position advanced vis-à-vis the second operating position from FIG. 4B in which the contact element has triggered a second threshold of the double-threshold sensor unit and moreover a pressure sensor is triggered.

Since the pressure sensor 22A disposed behind the diaphragm plate 22 is not yet pressed sufficiently strongly by the piston plate 18, the two fixing brackets 20A and 20B of the fixing means 20 are still in the open position (FIG. 4B).

Hereinafter, the functional connections of the present drive device 1 are explained in detail especially regarding the FIGS. 4, 5, 6 and 7. The drive device 1 comprises a blocking means 51 automatically releasable by the multi-threshold sensor unit 24 for blocking manual infeed motion of the drive head unit 3 in the piston driving direction 10, wherein advantageously the blocking means 51 directly comprises the multi-part advancing spindle nut 9.

The blocking means 51 includes an axially displaceable operating element 52 which in this case comprises at least one axially displaceable triggering sleeve 53 by way of example that is arranged concentrically around the two nut shells 12 and 13 of the advancing spindle nut 9. The triggering sleeve 53 is movably supported in the longitudinal extension 11 of the advancing spindle 8 radially outside of the advancing spindle nut 9.

So that the blocking means 51 can be activated extremely quickly it exhibits means 54 for accelerating the triggering sleeve 53, the accelerating means 54 being configured in a structurally simple manner by a coil spring 55 which in turn is supported radially outside of the triggering sleeve 53.

Furthermore, the operating element 52 includes a releasing sleeve 56 which may equally be disposed to be axially movable and concentric around the two nut shells 12 and 13 of the advancing spindle nut 9.

In this respect, the two sliding sleeves 53 and 56 are also supported to be axially movable with respect to the longitudinal extension 57 of the two radially movable nut shells 12 and 13.

Figure 5A:
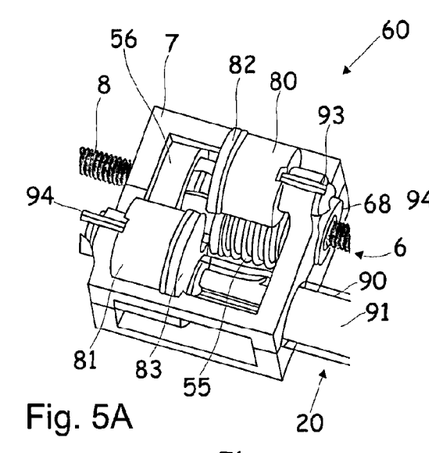
FIG. 5A schematically shows a detail view of the advancing means in the first operating position as regards FIG. 4A.
Figure 5B:
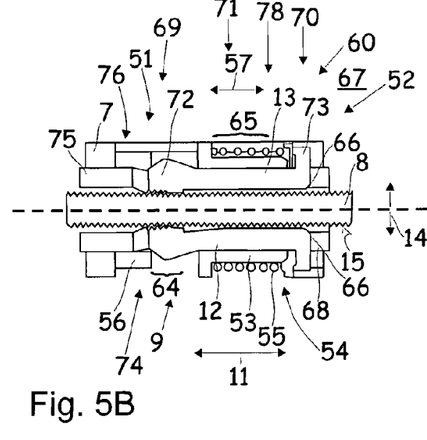
FIG. 5B schematically shows a view of a longitudinal section of the detail view from FIG. 5A.

For better comprehension of the functioning of the present operating element 52 of the advancing spindle nut 9 in connection with the function of the multi-threshold sensor unit 24, in FIGS. 4A, 5A and 5B a first operating position 60 of the drive device 1 is exemplified in which the two nut shells 12 and 13 are not in positive engagement with the male thread 15 of the advancing spindle 8. In said first operating position 60 the drive head unit 3 can be manually moved more quickly toward the piston plate 18 with a manual infeed motion in the piston driving direction 10 (FIG. 4A). The transmitter element 27 is still provided ahead of the two light barriers 29 and 30. So far the advancing spindle nut 9 is still opened, as this is also schematically represented on the far right in the representation according to FIG. 4A. This operating position 60 can especially be chosen when the infusion syringe is replaced at the infusion pump 2.

Figure 6A:
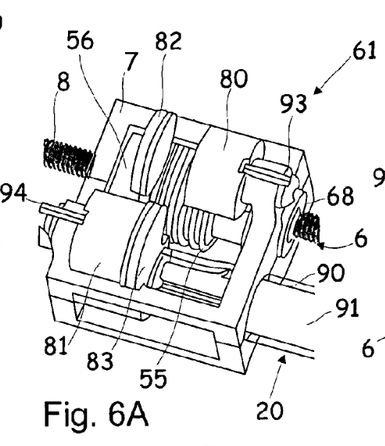
FIG. 6A schematically shows a detail view of the advancing means in the second operating position as regards FIG. 4B.
Figure 6B:
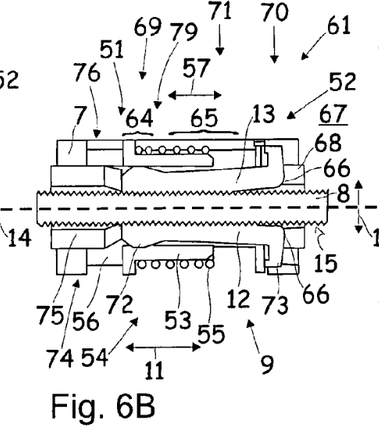
FIG. 6B schematically shows a view of a longitudinal section of the detail view from FIG. 6A.

In a second operating position 61 exemplified in the FIGS. 4B, 6A and 6B the transmitter element 27 is displaced already into the first light barrier 29, thereby the blocking means 51 being triggered. The advancing means 6 is now blocked as such by the radially engaged advancing spindle nut 9 so that no further manual infeed motion of the drive head unit 3 in the piston driving direction 10 is possible. In this respect, the risk is excluded that the diaphragm plate 22 critically abuts against the piston plate 18 and consequently bolus administration possibly dangerous to a patient is inadvertently carried out. The piston plate 18 does not yet press onto the pressure sensor 22A behind the diaphragm plate 22 so that the fixing brackets 20A and 20B are still opened.

Figure 7A:
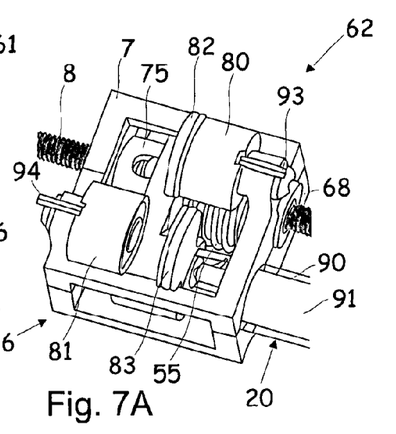
FIG. 7A schematically shows a detail view of the advancing means in the third operating position as regards FIG. 4C.
Figure 7B:
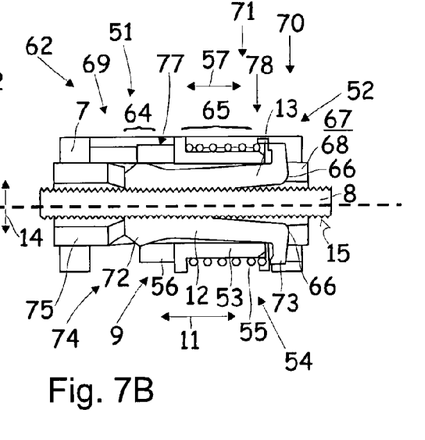
FIG. 7B schematically shows a view of a longitudinal section of the detail view from FIG. 7A.

Finally, in a further third operating position 62 chosen by way of example regarding the FIGS. 4C, 7A and 7B the drive device 1 is in basic operation in which the pressure sensor 22A is pressed sufficiently strongly by the piston plate 18, thereby the fixing brackets 20A and 20B being closed. The drive head unit 3 is now successively driven by the advancing means 6 in the piston driving direction 10. Thus a desired infusion therapy can be executed in a way known per se with the infusion pump 2.

Considering the representations of all FIGS. 5, 6 and 7 it is clearly evident that each of the two radially movable nut shells 12 and 13 has an engaging area 64 for engaging in the male thread 15 of the advancing spindle 8. In so far a positive connection between the nut shells 12 and 13 of the advancing spindle nut 9 and the male thread 15 of the advancing spindle 8 can be produced above the respective engaging area 64 of the nut shells 12 and 13, resp., when said engaging area 64 is properly moved radially in the direction of the advancing spindle 8 or is retained. The two nut shells 12, 13 then are engaged vis-à-vis the advancing spindle 8. This is the case, for example, with the two operating positions 61 and 62. Moreover, the two radially movable nut shells 12 and 13 further include a supporting area 65 with which the nut shells 12 and 13 at most can radially rest on the male thread 15 but cannot engage with the same. The engaging area 64 and the supporting area 65 are arranged axially in series.

In order to be able to radially incline each of the two radially movable nut shells 12, 13 with the two sliding sleeves 53, 56 vis-à-vis the advancing spindle 8 around a tilting axis 66 extending substantially transversely to the longitudinal extension 57 of the respective nut shell 12 and 13, resp., each of the two nut shells 12 and 13 is supported at its end side 67 on an advancing slide bearing 68. According to the representation of the FIGS. 5B, 6B and 7B, the tilting axis 66 extends normal to the drawing plane.

Moreover, the advancing spindle nut 9 includes a head area 69 and a foot area 70 the respective outer diameters of which are larger than an interposed advancing spindle nut zone 71, the head area 69 forming a slide-on ramp 72 for the two axially movable sliding sleeves 53 and 56 and the foot area 70 forming a counter-bearing 73 for the two axially movable sliding sleeves 53 and 56.

At an advancing spindle nut end 74 facing the advancing slide bearing 68 a parking means 75 supported on the advancing slide 7 for the release sleeve 56 is provided, wherein the parking means 75 is placed axially adjacent to the advancing spindle nut 9. When the release sleeve 56 is slipped onto the seat of the parking means 75 and is parked adjacent to the advancing spindle nut 9, the release sleeve 56 is provided in an opening position 76. This is the case with the two operating positions 60 and 61. In the third operating position 62 the release sleeve 56 is shifted onto the ramp 72 and is accordingly provided in a closing position 77.

The release sleeve 53 is provided in each of the two operating positions 60 and 62 in its own opening position 78 in which the trigger sleeve 53 is closer to the counter-bearing 73 than to the ramp 72. Merely in the operating position 61 the trigger sleeve 53 is provided in a closing position 79 assigned thereto.

Moreover, the advancing means 8 comprises a first holding solenoid 80 and a second holding solenoid 81 arranged above the advancing slide 7 in this embodiment.

The first holding solenoid 80 is associated with the release sleeve 53 and accordingly it may correspond to a magnetic plate 82 of the release sleeve 53. For this purpose, the magnetic plate 82 is placed ahead of the first holding solenoid 80 and is axially movably supported while being coupled to the release sleeve 53. In the two operating positions 60 and 62 the first holding solenoid 80 is supplied with current so that it can keep contact to the magnetic plate 82 and thus can also maintain the release sleeve 53 in its opening position 78. In the second operating position 61 the magnetic plate 82 is spaced apart from the first holding solenoid 80 to which no current is supplied.

Accordingly, the second holding solenoid 81 is associated with the release sleeve 56 and it may correspond to a magnetic plate 83 of the release sleeve 56, said magnetic plate 83 being placed ahead of the second holding solenoid 81 for this purpose. The magnetic plate 83 is axially displaced jointly with the release sleeve 56, as it is coupled thereto. In this respect, in the operating positions 60 and 61 the magnetic plate 83 is in contact with the second holding solenoid 81 supplied with current, while in the second operating position 62 it is arranged remote from the second holding solenoid 81 which is not supplied with current.

When a replacement of the infusion syringe is desired or necessary, the infusion is stopped. Subsequently the operating lever 36 at the drive head unit 3 is actuated. By actuating the operating lever 36 the spring 92 loaded release sleeve 56 is moved in the direction of the second holding solenoid 81 by the retaining arm 16 designed as a tube 90 (FIG. 3) via an inner fixing shaft 91. Said actuation is additionally established by a micro-switch comprising a sensor not shown here, thereby the two holding solenoids 80 and 81 being supplied with current via appropriate electric cables 93 and 94 and the two sliding sleeves 53 and 56 consequently being separated from each other. Accordingly, the two nut shells 12 and 13 open. Also the fixing brackets 20A and 20B of the fixing means 20 open due to the actuation of the operating lever 36. The form closure between the advancing spindle 8 and the advancing spindle nut 9 is reversed according to the first operating position 60 and the drive head unit 3 can be brought into a deployed position (FIG. 4A) opposite to the piston driving direction 10.

Subsequently, the clamping bracket 43 is opened and appropriately swiveled so that the seat 42 is easily accessible. A potentiometer 97 mounted inside the infusion pump housing 35 identifies the state of the clamping bracket 43 (FIG. 1). The infusion syringe to be replaced can be removed and the new infusion syringe 5 can be inserted into the seat 42. The infusion syringe wings of the infusion syringe 5 to be inserted are secured to the clamping lug 44 so that the new infusion syringe 5 is axially fixed to the infusion syringe pump 2. In this context, also the clamping bracket 43 is closed again so that the infusion syringe 5 is also radially fixed. The potentiometer 97 at the clamping bracket 43 directly measures the infusion syringe diameter.

Now the drive head unit 3 can be guided toward the piston plate 18 in accordance with the fill level of the infusion syringe 5 and thus also the position of the infusion syringe piston 4. So that larger distances between the drive head unit 3 and the piston plate 18 can be overcome more quickly, this can be performed by manual infeed motion in the piston driving direction 10, as the two radially movable nut shells 12 and 13 are not engaged in the male thread 15 of the advancing spindle 8, as this is shown in the first operating position 60 according to FIGS. 4A, 5A and 5B. In the first operating position 60 the two holding solenoids 80 and 81 are supplied with current, the sliding sleeves 53 and 56 are arranged to be separated from each other and the two nut shells 12 and 13 are radially opened. Moreover, the fixing means 20 at the drive head unit 3 is opened.

As soon as the contact element 27A enters into contact with the piston plate 22 (FIG. 4B), the transmitter element 27 especially moves inwardly into the drive head unit 3. Inside the drive head unit casing 3A the transmitter element 27 successively passes the two light barriers 29 and 30 of the multi-threshold sensor unit 24.

When passing the first light barrier 29 (FIG. 4B) the current supply to the first holding solenoid 80 is disconnected and the release sleeve 53 springs over the ramps 72 of the two radially movable nut shells 12 and 13 with the further spring 92, thereby the advancing spindle nut 9 suddenly positively engaging with the engaging areas 64 in the male thread 15 of the advancing spindle 8. Thus the advancing means 6 blocks, as is represented in the second operating position 61 according to FIGS. 4B, 6A and 6B. Manual infeed motion in the piston driving direction 10 is suddenly suppressed hereby.

However, the advancing means 6 now automatically continues traveling until the transmitter element 27 passes the second light barrier 30 (FIG. 4C). The second light barrier 30 is required here as the change of position of the radially closed and thus radially engaged nut shells 12 and 13 with their engaging areas 64 vis-à-vis the advancing spindle 8 is dependent on the reaction rate of the first holding solenoid 80 and the motion speed of the drive head unit 3 up to the piston plate 18. It is further possible that upon closing the advancing spindle nut 9 the two radially movable nut shells 12 and 13 merely rest on the thread flanks of the male thread 15 and the engaging area 64 of the advancing spindle nut 9 thus is not efficiently engaged in the male thread 15. However, by a short travel up to the second light barrier 30 the advancing spindle nut 9 can properly engage in the advancing spindle 8. Upon reaching the second light barrier 30 the linear position of the drive device 1 is then defined.

With this reference travel in accordance with the invention the advancing means 6 is provided in the second operating position 61 in which the first holding solenoid 80 is currentless, but the second holding solenoid 81 is supplied with current. Both sliding sleeves 53 and 56 are displaced to the left in the advancing slide 7 and the two nut shells 12 and 13 are radially closed. The fixing means 20 at the drive head unit 3 is still opened (FIG. 4B).

The drive head unit 3 traces the aligned path from the second light barrier 30 to the diaphragm plate 22 and the pressure sensor 22A arranged there behind with which correct bearing of the piston plate 18 on the main bearing surface 19 is detected and signaled at the drive head unit (FIG. 4C).

The second holding solenoid 81 is switched to be currentless, the release sleeve 56 is displaced into its closing position 77 (FIGS. 7A and 7B), the fixing means 20 closes and the fixing brackets 20A and 20B bear on the piston plate 18 of the infusion syringe 5 with form and force closure. The infusion syringe 5 is now caught safely and free from play (FIG. 4C).

With the clamping bracket 43 and the potentiometer 97 already the infusion syringe diameter has been measured so that on a display (not shown here) of the infusion pump 2 a selection of appropriate infusion syringes 5 is suggested. After confirmation of the valid infusion syringe 5 the desired infusion therapy can be entered and the infusion can now be started, wherein the drive head unit 3 and the advancing means 6 are provided in the third operating position 62 according to FIGS. 4C, 7A and 7B. In the third operating position 62 the advancing means 6 is thus locked. This means that the two holding solenoids 80, 81 are currentless.

It is especially advantageous that here a powerless state is provided regarding the two holding solenoids 80, 81 so that functioning of the third operating state 62 can be ensured even without supplying the holding solenoids 80, 81 with current.

The two sliding sleeves 53, 56 are displaced to the right within the advancing slide 7, as the further spring 92 is designed to be stronger than the coil spring 55. The two nut shells 12 and 13 remain radially closed just as the fixing means 23 at the drive head unit 3 is closed.

For switching the holding solenoids 80 and 81 especially quickly to be currentless, the drive device 1 advantageously further comprises a comparator circuit unit 100 (FIG. 1). Since the respective magnetic field of the holding solenoids 80 and 81 is generated with the aid of current supply, it is of advantage when a short-term overvoltage is admitted for rapid dying of the current supply. The comparator circuit unit 100 achieves an especially rapid drop of the energy state at the respective holding solenoid 80 and 81 so that the reaction time for blocking the advancing means 6 can be further reduced.

It is understood that the afore-explained embodiment merely is a first configuration of the drive device according to aspects of the invention. In so far the configuration of the invention is not restricted to this embodiment.

All features disclosed in the application documents are claimed as being essential to the invention, if they are novel vis-à-vis the state of the art either individually or in combination.

The invention claimed is:

1. A drive device for linear movement of an infusion syringe piston of an infusion syringe arranged at an infusion pump comprising:
    a drive head unit including a main bearing means for supporting a piston plate of the infusion syringe piston, a fixing means for fixing the infusion syringe piston on the main bearing means as well as means for triggering the fixing means; and
    an advancing means for the drive head unit including a motor-drivable advancing spindle and a multi-part advancing spindle nut including at least one radially movable nut shell, wherein the drive head unit in addition comprises detecting means for detecting the infusion syringe piston ahead of the main bearing means;
    wherein the detecting means includes a multi-threshold sensor unit having an at least two-stage upstream detection means for detecting different positions of the infusion syringe piston before a piston plate of the infusion syringe piston enters into contact with the main bearing means.

2. The drive device according to claim 1, wherein the multi-threshold sensor unit includes at least two sensors to be triggered by means of one single transmitter element, said transmitter element comprising a contact element projecting from the main bearing means.

3. The drive device according to claim 1, wherein the detecting means comprises at least two light barriers which are arranged axially in series within the drive head unit.

4. The drive device according to claim 3, wherein at least either of the two light barriers is a fork light barrier.

5. The drive device according to claim 1, wherein the multi-threshold sensor unit includes at least one sensor element and wherein the main bearing means includes a diaphragm plate comprising a transmitter element including a contact element configured to trigger the at least one sensor element of the multi-threshold sensor unit.

6. The drive device according to claim 1, further comprising a single transmitter element arranged inside the means for triggering the fixing means, said single transmitter element comprising a contact element projecting from the main bearing means.

7. The drive device according to claim 1, further comprising a single transmitter element including a contact element projecting from the main bearing means, the single transmitter element configured to travel a distance between 2 mm and 10 mm before a first stage of the two-stage upstream detection means can be triggered by the single transmitter element.

8. The drive device according to claim 7, wherein the distance is 4 mm.

9. The drive device according to claim 1, wherein the drive device further comprises:
- at least one single transmitter element comprising a contact element projecting from the main bearing means,
- a first sensor element,
- a second sensor element, and
- at least one joint control means operating as a function of the detecting means for automatic radial engagement of the at least one radially movable nut shell with the advancing spindle and for initiating travel of the main bearing means a distance to be carried out by means of the radially engaged advancing spindle nut, the distance predefined by initiation at contact by the contact element with the second sensor element and by concluding at contact by the main bearing means with the piston plate.

10. The drive device according to claim 9, wherein the drive device further comprises:
- holding solenoids,
- axially moveable sliding sleeves, and wherein
- the joint control means comprises a comparator circuit unit configured to switch the holding solenoids by altering a current supply to the holding solenoids such that the axially moveable sliding sleeves for radially engaging the at least one radially moveable nut shell are actuated by the holding solenoids.

11. The drive device according to claim 1, wherein the drive device further comprises axially moveable sliding sleeves for radially engaging the advancing spindle nut connected to the advancing spindle via a male thread, and wherein the advancing means comprises holding solenoids controllable by the detecting means, the holding solenoids configured to actuate the axially moveable sliding sleeves such that the advancing spindle nut connected to the advancing spindle via the male thread is radially engaged.

12. An infusion pump comprising the drive device according to claim 1.

13. A method for start-up of an infusion syringe on an infusion pump comprising a drive head unit for linear movement of an infusion syringe piston in which at least one radially movable nut shell of an advancing spindle nut is radially disengaged from an advancing spindle of an advancing means for driving the drive head unit so that the drive head unit of a piston plate of the infusion syringe piston can be quickly axially fed by hand and in which for preventing inadvertent bolus administration the piston plate can be detected by a detecting means including a multi-threshold sensor unit and an at least two-stage upstream detection means associated with the drive head unit, before the piston plate enters into contact with a main bearing surface of a main bearing means of the drive head unit, wherein
- in a first detecting step a contact element of the detecting means triggers a first sensor element, thereby the manual feeding of the drive head unit by means of the advancing spindle nut and the advancing spindle is blocked by the at least one radially movable nut shell radially engaging the advancing spindle, wherein then the drive head unit of the piston plate is further fed by motor drive manner via the advancing means,
- in a second detecting step the contact element triggers a second sensor element, thereby a motor-driven travel of the drive head unit up to the main bearing surface of the main bearing unit being initiated, and
- in a third detecting step the motor-driven travel is stopped in the course of contact of the piston plate with the main bearing surface and retaining brackets of a fixing means for the piston plate are closed, thereby the piston plate being secured to the main bearing means.

14. The method according to claim 13, wherein as the drive head unit approaches the infusion syringe a manual infeed motion in a piston driving direction, the contact element triggers the first sensor element and subsequently triggers the second sensor element, and wherein the manual infeed motion in the piston driving direction of the drive head unit is blocked prior to the contact element triggering the second sensor element.

15. The method according to claim 13, wherein the motor-driven reference travel is carried out by way of a defined number of motor steps.

16. The drive device according to claim 1, wherein:
- the detecting means further comprises a contact element configured to trigger a first sensor element of the two-stage upstream detection means in a first detecting step before the piston plate enters into contact with the main bearing means, such that a manual infeed motion in a piston driving direction of the drive head unit is blocked by the radially moveable nut shell radially engaging the advancing spindle;
- the contact element is further configured to trigger a second sensor element of the two-stage upstream detection means in a second detecting step that is subsequent to the first detecting step and is before the piston plate enters into contact with the main bearing means such that a motor-driven travel of the drive head unit up to a main bearing surface of the main bearing means is initiated;
- the fixing means for fixing the infusion syringe piston comprises retaining brackets; and
- the motor-driven travel of the drive head unit is configured to stop upon contact of the piston plate with the main bearing surface in a third detecting step, such that the retaining brackets of the fixing means are closed and the piston plate is secured to the main bearing means.

* * * * *